US008455399B2

(12) United States Patent
Maienfisch et al.

(10) Patent No.: US 8,455,399 B2
(45) Date of Patent: Jun. 4, 2013

(54) N-(4-PERFLUOROALKYL-PHENYL)-4-TRIAZOLYL-BENZAMIDES AS INSECTICIDES

(75) Inventors: Peter Maienfisch, Stein (CH); Christopher Richard Ayles Godfrey, Stein (CH); Pierre Joseph Marcel Jung, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/318,946

(22) PCT Filed: Apr. 14, 2010

(86) PCT No.: PCT/EP2010/054863
§ 371 (c)(1),
(2), (4) Date: Dec. 1, 2011

(87) PCT Pub. No.: WO2010/127927
PCT Pub. Date: Nov. 11, 2010

(65) Prior Publication Data
US 2013/0023571 A1    Jan. 24, 2013

(30) Foreign Application Priority Data
May 6, 2009    (GB) .................................. 0907823.9

(51) Int. Cl.
*A01N 43/653*    (2006.01)
*C07D 249/08*    (2006.01)
(52) U.S. Cl.
USPC ...................................... 504/272; 548/267.6
(58) Field of Classification Search
USPC ...................................... 504/272; 548/267.6
See application file for complete search history.

(56) References Cited

FOREIGN PATENT DOCUMENTS

| WO | 9504729 | 2/1995 |
|---|---|---|
| WO | 2008000438 | 1/2008 |
| WO | 2008074427 | 6/2008 |

OTHER PUBLICATIONS

Database ChemAbs [Online]; Chemical Abstracts Service, Columbus, Ohio, US; Jan. 25, 2008, XP007913716 retrieved from STN Database Accession No. 2042665018 CAS Registry No. 930462-65-0 in Ryan Scientific Screening Library.
Database ChemAbs [Online]; Chemical Abstracts Service, Columbus, Ohio, US; Jan. 25, 2008, XP007913717 retrieved from STN Database Accession No. 2043460461 CAS Registry No. 338407-82-2 in Ryan Scientific Screening Library.

*Primary Examiner* — Samantha Shterengarts
(74) *Attorney, Agent, or Firm* — Brian D. McAlhaney

(57) ABSTRACT

The present invention relates to novel triazole-substituted benzamide derivatives, to processes and intermediates for preparing them, to methods of using them to control insect, acarine, nematode and mollusc pests, and to insecticidal, acaricidal, nematicidal and molluscicidal compositions comprising them. Formula (I).

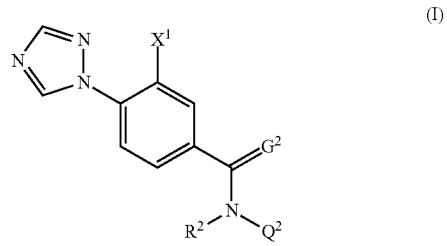

11 Claims, No Drawings

N-(4-PERFLUOROALKYL-PHENYL)-4-TRIAZOLYL-BENZAMIDES AS INSECTICIDES

This application is a 371 of International Application No. PCT/EP2010/054863 filed Apr. 14, 2010, which claims priority to GB 0907823.9 filed May 6, 2009, the contents of which are incorporated herein by reference.

The present invention relates to novel triazole-substituted benzamide derivatives, to processes and intermediates for preparing them, to methods of using them to control insect, acarine, nematode and mollusc pests, and to insecticidal, acaricidal, nematicidal and molluscicidal compositions comprising them.

Compounds having insecticidal properties are disclosed in EP 1,714,958, JP 2006/306771, WO 2006/137376, EP 1,916,236, WO 2007/017075, WO 2008/000438, WO 2008/074427 and WO 2009/049845. Amide derivatives having $5HT_{1D}$ receptor antagonist properties are disclosed for use as pharmaceuticals in WO 95/04729. There exists a need for alternative methods of control of pests. Preferably, new compounds may possess improved insecticidal properties, such as improved efficacy, improved selectivity, lower tendency to generate resistance or activity against a broader range of pests. Compounds may be more advantageously formulated or provide more efficient delivery and retention at sites of action, or may be more readily biodegradable.

It has now surprisingly been found that certain triazole-substituted benzamide derivatives have insecticidal properties.

Accordingly, the present invention provides a compound of formula (I)

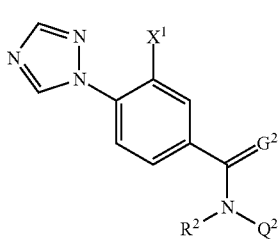

(I)

wherein $X^1$ is $NO_2$, $NH_2$, a group of formula (II) or a group of formula (III)

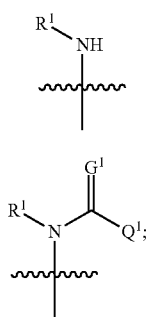

$G^1$ and $G^2$ are each independently oxygen or sulfur;

$Q^1$ is aryl or heterocyclyl, each optionally substituted by one to five $R^3$ substituents, which may be the same or different;

$R^1$ is hydrogen, $C_1$-$C_8$alkyl, $C_1$-$C_8$alkylcarbonyl, or $C_1$-$C_8$alkoxycarbonyl;

$R^2$ is hydrogen, $C_1$-$C_8$alkyl, $C_1$-$C_8$alkylcarbonyl, or $C_1$-$C_8$alkoxycarbonyl;

$R^3$ is halogen, cyano, nitro, $C_1$-$C_4$alkyl, $C_1$-$C_4$haloalkyl, $C_1$-$C_4$alkoxy, or $C_1$-$C_4$haloalkoxy;

$Q^2$ is a group of formula (IV)

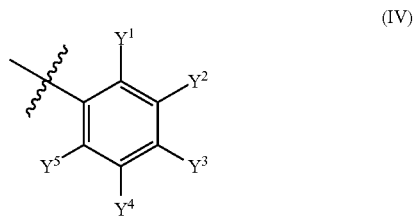

$Y^1$ and $Y^5$ are each independently selected from halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkoxy-$C_1$-$C_4$alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl;

$Y^3$ is selected from $C_2$-$C_6$perfluoroalkyl, $C_2$-$C_6$perfluorocycloalkyl, hydroxy-$C_2$-$C_6$perfluoroalkyl, $C_1$-$C_4$alkylcarbonyloxy-$C_2$-$C_6$perfluoroalkyl, $C_1$-$C_4$haloalkylcarbonyloxy-$C_2$-$C_6$perfluoroalkyl, $C_1$-$C_6$perfluoroalkylthio, $C_1$-$C_6$perfluoroalkylsulfinyl, $C_1$-$C_6$perfluoroalkylsulfonyl, arylcarbonyloxy-$C_2$-$C_6$perfluoroalkyl, and arylcarbonyloxy-$C_2$-$C_6$perfluoroalkyl in which the aryl group may be substituted by one to five $R^4$ groups, which may be the same or different;

$Y^2$ and $Y^4$ are each independently selected from hydrogen, halogen and $C_1$-$C_4$alkyl; and $R^4$ is halogen, cyano, nitro, $C_1$-$C_4$alkyl, $C_1$-$C_4$haloalkyl, $C_1$-$C_4$alkoxy or $C_1$-$C_4$haloalkoxy; or an agrochemically acceptable salt or N-oxides thereof.

The compounds of formula (I) may exist in different geometric or optical isomers (enantiomers and/or diastereoisomers) or tautomeric forms. This invention covers all such isomers and tautomers and mixtures thereof in all proportions as well as isotopic forms such as deuterated compounds.

Unless otherwise indicated, alkyl, on its own or as part of another group, such as alkoxy, alkylcarbonyl or alkoxycarbonyl, may be straight or branched chain and may contain from 1 to 8 carbon atoms, preferably 1 to 6, more preferably 1 to 4, and most preferably 1 to 3. Examples of alkyl include methyl, ethyl, n-propyl, iso-propyl, n-butyl, sec-butyl, iso-butyl and tert-butyl.

Hydroxyalkyl are alkyl groups, which are substituted by one or more hydroxy groups, and includes, for example, hydroxymethyl and 1,3-dihydroxypropyl.

Halogen means fluorine, chlorine, bromine or iodine.

Haloalkyl groups may contain one or more identical or different halogen atoms, and include, for example, difluoromethyl, trifluoromethyl, chlorodifluoromethyl, 2,2,2-trifluoroethyl and 2,2-difluoroethyl. Perfluoroalkyl groups are alkyl groups which are completely substituted with fluorine atoms and include, for example, trifluoromethyl, pentafluoroethyl, heptafluoroprop-2-yl and nonafluorobut-2-yl. Where a Perfluoroalkyl groups are alkyl groups which are completely substituted with fluorine atoms and include, for example, trifluoromethyl, pentafluoroethyl, heptafluoroprop-2-yl and nonafluoro-but-2-yl.

Hydroxyperfluoroalkyl groups are hydroxyalkyl groups which are substituted in every available position by a fluorine atom, and include, for example, hexafluoro-2-hydroxyprop-2-yl and octafluoro-2-hydroxybut-2-yl.

Cycloalkyl groups may be monocyclic or bicyclic and may preferably contain from 3 to 8 carbon atoms, more preferably 4 to 7, and most preferably 5 to 6, and include, for example, cyclopropyl, cyclobutyl, cyclohexyl and bicyclo[2.2.1]heptan-2-yl.

Perfluorocycloalkyl groups are cycloalkyl groups which are substituted in every available position by a fluorine atom, and include, for example, undecafluorocyclohexyl.

Aryl includes phenyl, naphthyl, anthracenyl, indenyl, phenanthrenyl and biphenyl, with phenyl being preferred.

Heteroaryl means a mono-, bi- or tricyclic, aromatic hydrocarbon, containing 3 to 14, preferably 4 to 10, more preferably 4 to 7, most preferably 5 to 6 ring-atoms, including 1 to 6, preferably 1 to 4, more preferably, 1, 2 or 3 heteroatoms independently selected from nitrogen, oxygen and sulfur. Examples include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuranyl, benzimidazolyl, benzothiadiazolyl, indazolyl, benzotriazolyl, benzothiazolyl, benzoxazolyl, quinolyl, isoquinolyl, phthalazinyl, quinoxalinyl, quinazolinyl, cinnolinyl and naphthyridinyl. Preferred, are monocyclic heteroaryl groups containing 4 to 7, preferably 5 to 6 ring-atoms, including 1, 2 or 3 heteroatoms independently selected from nitrogen, oxygen and sulfur.

Heterocyclyl, as used herein, includes heteroaryl, and in addition may be a saturated or partially unsaturated monocyclic or bicyclic hydrocarbon containing from 3 to 10 ring-atoms including 1 to 6, preferably 1 to 4, more preferably 1, 2 or 3 heteroatoms independently selected from nitrogen, oxygen and sulfur. Examples of non-aromatic heterocyclyl groups are oxiranyl, azetidinyl, tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, 1,3-dioxanyl, 1,4-dioxanyl, morpholinyl, dithianyl, thiomorpholinyl, piperazinyl, azepinyl, oxazepinyl, thiazepinyl, thiazolinyl, diazapanyl, 2,3-dihydrobenzofuranyl, 3,4-dihydro-2H-benzo[b][1,4]dioxepinyl, benzo[1,3]dioxolanyl and 2,3-dihydrobenzo[1,4]dioxinyl.

Preferred values of $X^1$, $G^1$, $G^2$, $Q^1$, $R^1$, $R^2$, $R^3$, $Q^2$, $Y^1$, $Y^2$, $Y^3$, $Y^4$, $Y^5$ and $R^4$ are, in any combination, as set out below.

In a first preferred aspect of the invention, $X^1$ is $NO_2$.

In a second preferred aspect of the invention, $X^1$ is $NH_2$.

In a third preferred aspect of the invention, $X^1$ is a group of formula (II)

In a fourth preferred aspect of the invention, $X^1$ is a group of formula (III).

Preferably, $G^1$ is oxygen.

Preferably, $G^2$ is oxygen.

Preferably, $Q^1$ is aryl or heteroaryl; each optionally substituted by one to five $R^3$ substituents, which may be the same or different.

More preferably, $Q^1$ is selected from phenyl, biphenyl and a five to six-membered monocyclic heteroaryl group containing 1, 2 or 3 heteroatoms independently selected from nitrogen, oxygen and sulfur; each optionally substituted by one to five $R^3$ substituents, which may be the same or different.

Yet more preferably, $Q^1$ is selected from phenyl, biphenyl, furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothienyl, benzofuranyl, benzimidazolyl, benzothiadiazolyl, indazolyl, benzotriazolyl, benzothiazolyl, benzoxazolyl, quinolyl, isoquinolyl, phthalazinyl, quinoxalinyl, quinazolinyl, cinnolinyl and naphthyridinyl; each optionally substituted by one to five $R^3$, and more preferably by one to three $R^3$ substituents, which may be the same or different.

Even more preferably, $Q^1$ is selected from phenyl, biphenyl, furanyl, pyridyl, thienyl, thiadiazolyl, oxazolyl, isoxazolyl, thiazolyl, isothiazolyl, pyrazolyl and pyrimidinyl; each optionally substituted by one to three $R^3$ substituents, which may be the same or different.

Even more preferably, $Q^1$ is phenyl, optionally substituted by one to three $R^3$ substituents, which may be the same or different.

Preferably, $R^3$ is selected from cyano, nitro, fluoro, chloro, bromo, iodo, methyl, ethyl, isopropyl, tert-butyl, trifluoromethyl, methoxy and trifluoromethoxy.

Most preferably, $R^3$ is selected cyano, nitro, chloro, fluoro and methyl.

Most preferably, $Q^1$ is selected from 4-cyanophenyl, 4-fluorophenyl, 2-methyl-3-nitrophenyl and 2-chloro-4-fluorophenyl.

Preferably, $R^1$ is hydrogen, methyl or ethyl and most preferably, hydrogen.

Preferably, $R^2$ is hydrogen.

Preferably, $Y^1$ is halogen, cyano, $C_1$-$C_4$alkyl, $C_1$-$C_4$alkoxy, $C_1$-$C_4$alkoxy-$C_1$-$C_4$alkyl or $C_1$-$C_3$alkylthio. More preferably, $Y^1$ is fluoro, chloro, bromo, cyano, methyl, ethyl, methoxy, methylthio, or methoxymethyl. Most preferably, $Y^1$ is chloro, bromo, methyl, ethyl, or cyano.

Preferably, $Y^2$ is hydrogen, chloro, fluoro or methyl. More preferably, $Y^2$ is hydrogen or fluoro. Most preferably, $Y^2$ is hydrogen.

Preferably, $Y^3$ is $C_2$-$C_6$perfluoroalkyl. More preferably, $Y^3$ is heptafluoropropyl or nonafluorobutyl. Yet more preferably, $Y^3$ is heptafluoroprop-2-yl or nonafluorobut-2-yl.

Preferably, $Y^4$ is hydrogen, chloro, fluoro or methyl. More preferably, $Y^4$ is hydrogen or fluoro. Most preferably, $Y^4$ is hydrogen.

Preferably, $Y^5$ is halogen, cyano, $C_1$-$C_4$alkyl, $C_1$-$C_4$alkoxy, $C_1$-$C_4$alkoxy-$C_1$-$C_4$alkyl or $C_1$-$C_3$alkylthio. More preferably, $Y^5$ is fluoro, chloro, bromo, cyano, methyl, ethyl, methoxy, methylthio, or methoxymethyl. Most preferably, $Y^5$ is chloro, bromo, methyl, ethyl, or cyano.

Preferably, $R^4$ is chloro, fluoro, cyano, nitro, methyl, ethyl, trifluoromethyl, methoxy, or trifluoromethoxy.

Preferably, $Q^2$ is 2,6-dimethyl-4-(heptafluoroprop-2-yl)phenyl, 2,6-diethyl-4-(heptafluoroprop-2-yl)phenyl, 2-ethyl-6-methyl-4-(nonafluorobut-2-yl)phenyl, 2,6-dibromo-4-(nonafluorobut-2-yl)phenyl, 2-bromo-6-chloro-4-(nonafluoro-but-2-yl)phenyl, or 2,6-dichloro-4-(nonafluorobut-2-yl)phenyl.

Most preferably, $Q^2$ is 2,6-dimethyl-4-(heptafluoroprop-2-yl)phenyl, 2,6-diethyl-4-(heptafluoroprop-2-yl)phenyl, 2-ethyl-6-methyl-4-(nonafluorobut-2-yl)phenyl, 2,6-dibromo-4-(nonafluorobut-2-yl)phenyl.

In a preferred embodiment of the first aspect of the invention, $X^1$ is $NO_2$.

$G^2$ is oxygen;

R² is hydrogen;
Y¹ is fluoro, chloro, bromo, cyano, methyl, ethyl, methoxy, methylthio, or methoxymethyl;
Y² and Y⁴ are both hydrogen;
Y³ is heptafluoroprop-1-yl, heptafluoroprop-2-yl, nonafluorobut-2-yl or undecafluorocyclohexyl; and
Y⁵ is fluoro, chloro, bromo, cyano, methyl, ethyl, methoxy, methylthio, or methoxymethyl.

In a more preferred embodiment of the first aspect of the invention,
X¹ is NO₂.
G² is oxygen;
R² is hydrogen; and
Q² is 2,6-dimethyl-4-(heptafluoroprop-2-yl)phenyl, 2,6-diethyl-4-(heptafluoroprop-2-yl)phenyl, 2-ethyl-6-methyl-4-(nonafluorobut-2-yl)phenyl, 2,6-dibromo-4-(nonafluorobut-2-yl)phenyl, 2-bromo-6-chloro-4-(nonafluoro-but-2-yl)phenyl, or 2,6-dichloro-4-(nonafluoro-but-2-yl)phenyl.

In a preferred embodiment of the second aspect of the invention,
X¹ is NH₂;
G² is oxygen;
R² is hydrogen;
Y¹ is fluoro, chloro, bromo, cyano, methyl, ethyl, methoxy, methylthio, or methoxymethyl;
Y² and Y⁴ are both hydrogen;
Y³ is heptafluoroprop-1-yl, heptafluoroprop-2-yl, nonafluorobut-2-yl or undecafluorocyclohexyl; and
Y⁵ is fluoro, chloro, bromo, cyano, methyl, ethyl, methoxy, methylthio, or methoxymethyl.

In a more preferred embodiment of the second aspect of the invention,
X¹ is NH₂;
G² is oxygen;
R¹ and R² are both hydrogen; and
Q² is 2,6-dimethyl-4-(heptafluoroprop-2-yl)phenyl, 2,6-diethyl-4-(heptafluoroprop-2-yl)phenyl, 2-ethyl-6-methyl-4-(nonafluorobut-2-yl)phenyl, 2,6-dibromo-4-(nonafluorobut-2-yl)phenyl, 2-bromo-6-chloro-4-(nonafluoro-but-2-yl)phenyl, or 2,6-dichloro-4-(nonafluoro-but-2-yl)phenyl.

In a preferred embodiment of the third aspect of the invention,
X¹ is a group of formula (II)
G² is oxygen;
R² is hydrogen;
Y¹ is fluoro, chloro, bromo, cyano, methyl, ethyl, methoxy, methylthio, or methoxymethyl;
Y² and Y⁴ are both hydrogen;
Y³ is heptafluoroprop-1-yl, heptafluoroprop-2-yl, nonafluorobut-2-yl or undecafluorocyclohexyl; and
Y⁵ is fluoro, chloro, bromo, cyano, methyl, ethyl, methoxy, methylthio, or methoxymethyl.

In a more preferred embodiment of the third aspect of the invention, X¹ is a group of formula (II)
X¹ is NH₂;
G² is oxygen;
R¹ and R² are both hydrogen; and
Q² is 2,6-dimethyl-4-(heptafluoroprop-2-yl)phenyl, 2,6-diethyl-4-(heptafluoroprop-2-yl)phenyl, 2-ethyl-6-methyl-4-(nonafluorobut-2-yl)phenyl, 2,6-dibromo-4-(nonafluorobut-2-yl)phenyl, 2-bromo-6-chloro-4-(nonafluoro-but-2-yl)phenyl, or 2,6-dichloro-4-(nonafluoro-but-2-yl)phenyl.

In a preferred embodiment of the fourth aspect of the invention,
X¹ is a group of formula (III);
G¹ and G² are both oxygen;
R¹ and R² are both hydrogen;
Q¹ is phenyl, optionally substituted by one to three R³ substituents, which may be the same or different;
R³ is selected from cyano, nitro, fluoro, chloro, bromo, iodo, methyl, ethyl, isopropyl, tert-butyl, trifluoromethyl, methoxy and trifluoromethoxy.
Y¹ is fluoro, chloro, bromo, cyano, methyl, ethyl, methoxy, methylthio, or methoxymethyl;
Y² and Y⁴ are both hydrogen;
Y³ is heptafluoroprop-1-yl, heptafluoroprop-2-yl, nonafluorobut-2-yl or undecafluorocyclohexyl; and
Y⁵ is fluoro, chloro, bromo, cyano, methyl, ethyl, methoxy, methylthio, or methoxymethyl.

In a more preferred embodiment of the fourth aspect of the invention,
X¹ is a group of formula (III);
G¹ and G² are both oxygen;
R¹ and R² are both hydrogen;
Q¹ is 4-cyanophenyl, 4-fluorophenyl, 2-methyl-3-nitrophenyl or 2-chloro-4-fluorophenyl.
Q² is 2,6-dimethyl-4-(heptafluoroprop-2-yl)phenyl, 2,6-diethyl-4-(heptafluoroprop-2-yl)phenyl, 2-ethyl-6-methyl-4-(nonafluorobut-2-yl)phenyl, 2,6-dibromo-4-(nonafluorobut-2-yl)phenyl, 2-bromo-6-chloro-4-(nonafluoro-but-2-yl)phenyl, or 2,6-dichloro-4-(nonafluoro-but-2-yl)phenyl.

Most preferred compounds of formula (I) are selected from
N-[2,6-dibromo-4-(1,2,2,3,3,3-hexafluoro-1-trifluoromethylpropyl)phenyl]-3-nitro-4-(1,2,4-triazol-1-yl)benzamide;
3-amino-N-[2,6-dibromo-4-(1,2,2,3,3,3-hexafluoro-1-trifluoromethylpropyl)-phenyl]-4-(1,2,4-triazol-1-yl)benzamide;
3-(4-cyanobenzoylamino)-N-[2,6-dibromo-4-(1,2,2,3,3,3-hexafluoro-1-trifluoromethylpropyl)phenyl]-4-(1,2,4-triazol-1-yl)benzamide;
3-(2-methyl-3-nitrobenzoylamino)-N-[2-ethyl-4-(1,2,2,3,3,3-hexafluoro-1-trifluoromethylpropyl)-6-methylphenyl]-4-(1,2,4-triazol-1-yl)benzamide;
3-(2-chloro-4-fluorobenzoylamino)-N-[2-ethyl-4-(1,2,2,3,3,3-hexafluoro-1-trifluoromethylpropyl)-6-methylphenyl]-4-(1,2,4-triazol-1-yl)benzamide;
3-(4-cyanobenzoylamino)-N-[2-ethyl-4-(1,2,2,3,3,3-hexafluoro-1-trifluoromethyl-propyl)-6-methylphenyl]-4-(1,2,4-triazol-1-yl)benzamide;
3-(2-chloro-4-fluorobenzoylamino)-N-[2,6-dibromo-4-(1,2,2,3,3,3-hexafluoro-1-trifluoromethylpropyl)phenyl]-4-(1,2,4-triazol-1-yl)benzamide;
3-(2-methyl-3-nitrobenzoylamino)-N-[2,6-dibromo-4-(1,2,2,3,3,3-hexafluoro-1-trifluoromethylpropyl)phenyl]-4-(1,2,4-triazol-1-yl)benzamide;
3-(4-fluorobenzoylamino)-N-[2,6-diethyl-4-(1,2,2,2-tetrafluoro-1-trifluoromethylethyl)phenyl]-4-(1,2,4-triazol-1-yl)benzamide;
3-(4-fluorobenzoylamino)-N-[2,6-dimethyl-4-(1,2,2,2-tetrafluoro-1-trifluoromethyl-ethyl)phenyl]-4-(1,2,4-triazol-1-yl)benzamide;
3-(4-fluorobenzoylamino)-N-[2-ethyl-4-(1,2,2,3,3,3-hexafluoro-1-trifluoromethyl-propyl)-6-methylphenyl]-4-(1,2,4-triazol-1-yl)benzamide; and
3-(4-fluorobenzoylamino)-N-[2,6-dibromo-4-(1,2,2,3,3,3-hexafluoro-1-trifluoromethylpropyl)phenyl]-4-(1,2,4-triazol-1-yl)benzamide.

The compounds of the invention may be made by the methods shown in Scheme 1 and Scheme 2.

Scheme 1

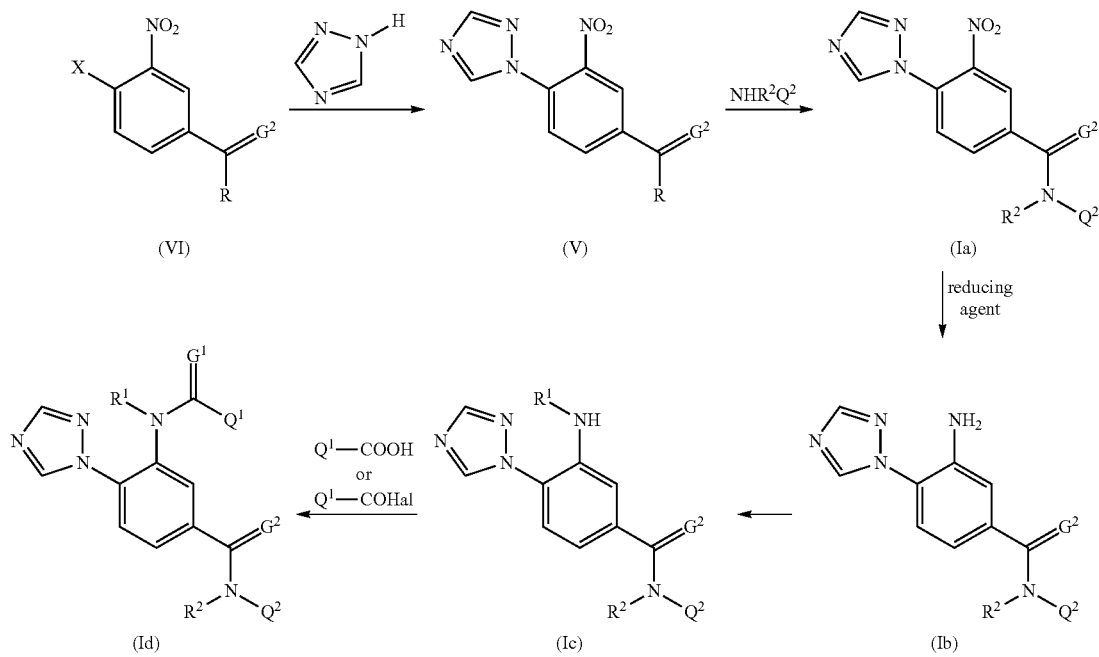

1) Compounds of formula (V) wherein $G^2$ is oxygen can be made from a compound of formula (VI) wherein $G^2$ is oxygen and X is halogen, such as fluorine or chlorine, by reaction with 1H-1,2,4-triazole. The presence of the nitro group facilitates the displacement of the leaving group by 1H-1,2,4-triazole.

2) Compounds of formula (Ia) wherein $G^2$ is oxygen can be made from a compound of formula (V) wherein $G^2$ is oxygen and R is OH, Cl, or $C_1$-$C_6$alkoxy, via acylation with an amine of formula $NHR^2Q^2$. When R is OH the reaction may be conducted in the presence of a coupling reagent, such as N,N'-dicyclohexylcarbodiimide ("DCC"), 1-ethyl-3-[3-dimethyl-amino-propyl]carbodiimide hydrochloride ("EDC") or bis(2-oxo-3-oxazolidinyl)phosphonic chloride ("BOP—Cl"), in the presence of a base and optionally in the presence of a nucleophilic catalyst, such as hydroxybenzotriazole. When R is Cl, the reaction may be conducted in the presence of a base and optionally in the presence of a nucleophilic catalyst. Suitable bases include, for example, pyridine, triethylamine, 4-(dimethylamino)pyridine or diisopropylethylamine. When R is $C_1$-$C_6$alkoxy the ester may be converted directly to the amide by heating the ester and amine together in a thermal process.

3) Acid halides of formula (V) wherein $G^2$ is oxygen and R is Cl, F or Br may be made from carboxylic acids of formula (V) wherein $G^2$ is oxygen and R is OH, under standard conditions, such as treatment with thionyl chloride or oxalyl chloride.

4) Carboxylic acids of formula (V) wherein $G^2$ is oxygen and R is OH, may be formed from esters of formula (V) wherein $G^2$ is oxygen and R is $C_1$-$C_6$alkoxy, such as by treatment of the ester with an alkali hydroxide, such as sodium hydroxide, in a solvent, such as ethanol and/or water.

5) Compounds of formula (Ib) wherein $G^2$ is oxygen may be made by the reduction of a nitro compound of formula (Ia) wherein $G^2$ is oxygen, such as by treatment with iron metal powder or tin chloride under acidic conditions, or hydrogenation catalyzed by a noble metal such as palladium on carbon.

6) Compounds of formula (Ic) wherein $G^2$ is oxygen may be made from compounds of formula (Ib) by sequential treatment with an alcohol $R^1$—OH under acidic conditions and then formation of the N—$R^1$ bond. Alternatively, reactions based on oxidized versions of the alcohols such as the corresponding aldehydes and ketones or based on more activated analogues of the alcohols such as the corresponding halides or sulfonates may be used. For example, reductive amination may be achieved by treatment of the amine with an aldehyde or ketone and a reducing agent such as sodium cyanoborohydride or sodium borohydride. Alternatively, alkylation may be achieved by treating the amine with an alkylating agent such as an alkyl halide, optionally in the presence of a base. Alternatively, arylation may be achieved by treatment of the amine with an aryl halide or sulfonate in the presence of a suitable catalyst/ligand system, often a palladium(0) complex. Alcohols of formula $R^1$—OH are either commercially available or may be made by known methods known to a person skilled in the art.

7) Compounds of formula (Ia) wherein $G^1$ and $G^2$ are both oxygen can be made by treatment of a compound of formula (Ib) where $G^2$ is oxygen by acylation with a carboxylic acid of formula $Q^1$-COOH or an acid halide of formula $Q^1$-COHal, wherein Hal is Cl, F or Br, under standard conditions as described in 2).

8) Compounds of formula (Ia) wherein $G^1$ and $G^2$ are both sulfur can be made from a compound of formula (Ia) wherein $G^1$ and $G^2$ are both oxygen by treatment with a thio-transfer reagent such as Lawesson's reagent or phosphorus pentasulfide.

9) Compounds of formula (Ia) wherein $G^1$ is oxygen and $G^2$ is sulfur can be made by treating a compound of formula (Ib) wherein $G^2$ is oxygen with a thio-transfer reagent as defined under 8) prior to coupling with a carboxylic acid of formula Q¹-COOH or an acid halide of formula Q¹-COHal, wherein Hal is Cl, F or Br.

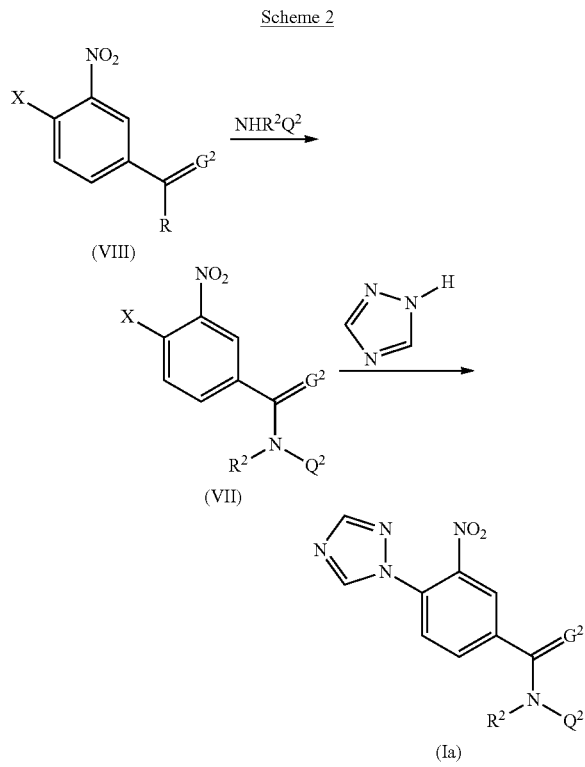

Scheme 2

10) Alternatively, compounds of formula (Ia) wherein $G^2$ is oxygen can be made from a compound of formula (VII) wherein $G^2$ is oxygen and X is halogen such as fluorine or chlorine by reaction with 1H-1,2,4-triazole. The presence of the nitro group facilitates the displacement of the leaving group by 1H-1,2,4-triazole.

11) Compounds of formula (VII) wherein $G^2$ is oxygen can be made from a compound of formula (VIII) wherein $G^1$ is oxygen and R is OH, Cl, or $C_1$-$C_6$alkoxy, via acylation with an amine of formula $NHR^2Q^2$ using standard reaction conditions as described under 2).

The compounds of formula (I) can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus,* and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects or acarines.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;
b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad, azadirachtin or spinetoram;
h) Hormones or pheromones;
i) Organochlorine compounds, such as endosulfan (in particular alpha-endosulfan), benzene hexachloride, DDT, chlordane or dieldrin;
j) Amidines, such as chlordimeform or amitraz;
k) Fumigant agents, such as chloropicrin, dichloropropane, methyl bromide or metam;
l) Neonicotinoid compounds, such as imidacloprid, thiacloprid, acetamiprid, nitenpyram, dinotefuran, sulfoxaflor, thiamethoxam, clothianidin, nithiazine or flonicamid;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr;
q) Pymetrozine;
r) Spirotetramat, spirodiclofen or spiromesifen;
s) Diamides, such as flubendiamide, chlorantraniliprole or cyantraniliprole;
t) Sulfoxaflor; or
u) Metaflumizone.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxyiminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

EXAMPLES

The following abbreviations are used in this section: s=singlet; bs=broad singlet; d=doublet; dd=double doublet; dt=double triplet; t=triplet; tt=triple triplet, q=quartet, sept=septet; m=multiplet; Me=methyl; Et=ethyl; Pr=propyl; Bu=butyl; M.p.=melting point; RT=retention time; MH$^+$=measured mass of the molecular cation.

The following LC-MS methods were used to characterize the compounds:

Method 1

| | |
|---|---|
| MS | ZQ Mass Spectrometer from Waters (Single quadrupole mass spectrometer), ionization method: electrospray, polarity: positive ionization, capillary (kV) 3.00, cone (V) 30.00, source temperature (° C.) 100, desolvation temperature (° C.) 250, cone gas flow (L/Hr) 50, desolvation gas flow (L/Hr) 400, mass range: 150 to 1000 Da. |
| LC | HP 1100 HPLC from Agilent: solvent degasser, quaternary pump, heated column compartment and diode-array detector. Column: Phenomenex Gemini C18, 3 μm particle size, 110 Angstrom, 30 × 3 mm, temperature (° C.) 60, DAD wavelength range (nm): 200 to 500, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Method 2

| | |
|---|---|
| MS | ZQ Mass Spectrometer from Waters (Single quadrupole mass spectrometer), ionization method: electrospray, polarity: positive or negative ionization, capillary (kV) 3.10, cone (V) 30.00, source temperature (° C.) 100, desolvation temperature (° C.) 250, cone gas flow (L/Hr) 50, desolvation gas flow (L/Hr) 400, mass range: 150 to 1000 Da. |
| LC | HP 1100 HPLC from Agilent: solvent degasser, binary pump, heated column compartment and diode-array detector. Column: Phenomenex Gemini C18, 3 μm particle size, 110 Angstrom, 30 × 3 mm, temperature (° C.) 60, DAD wavelength range (nm): 200 to 500, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Method 4

| | |
|---|---|
| MS | ZMD Mass Spectrometer from Micromass (Single quadrupole mass spectrometer), ionization method: electrospray, polarity: positive ionization, capillary (kV) 3.80, cone (V) 30.00, source temperature (° C.) 80, desolvation temperature (° C.) 200, desolvation gas flow (L/Hr) 600, mass range: 150 to 1000 Da. |
| LC | HP 1100 HPLC from Agilent: solvent degasser, binary pump, heated column compartment and wavelength detector. Column: Phenomenex Gemini C18, 3 μm particle size, 110 Angstrom, 30 × 3 mm, temperature (° C.) 60, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Method D

| MS | ZQ Mass Spectrometer from Waters (Single quadrupole mass spectrometer), ionization method: electrospray, polarity: positive ionization, capillary (kV) 3.00, cone (V) 30.00, source temperature (° C.) 150, desolvation temperature (° C.) 350, cone gas flow (L/Hr) 50, desolvation gas flow (L/Hr) 400, mass range: 150 to 1000 Da. |
|---|---|
| LC | HP 1100 HPLC from Agilent: solvent degasser, quaternary pump, heated column compartment and diode-array detector. Column: Phenomenex Gemini C18, 3 μm particle size, 110 Angstrom, 30 × 3 mm, temperature (° C.) 60, DAD wavelength range (nm): 200 to 500, solvent gradient: A = water + 0.05% formic acid, B = acetonitrile/methanol (4:1, v/v) + 0.04% formic acid. |

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.10 | 95.0 | 5.0 | 1.700 |

Example I1

2,6-dibromo-4-(1,2,2,3,3,3-hexafluoro-1-trifluoromethylpropyl)phenylamine

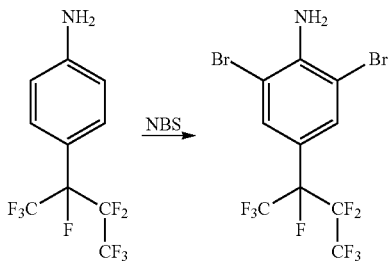

4-(1,2,2,3,3,3-Hexafluoro-1-trifluoromethylethyl)phenylamine (prepared according to EP 1,006,102) (56 g, 180 mmol) was dissolved in dichloromethane (500 ml) and N-bromo-succinimide ("NBS") (76.9 g, 432 mmol) was added. The reaction mixture was stirred at ambient temperature for 2 hours. The reaction mixture was concentrated and the residue partitioned between ethyl acetate (200 ml) and water (200 ml). The phases were separated and the aqueous phase was extracted twice with ethyl acetate. The combined organic extracts were dried over sodium sulfate and concentrated. The residue was purified by column chromatography on silica gel (eluent: cyclohexane/ethyl acetate 8:2) to give 2,6-dibromo-4-(1,2,2,3,3,3-hexafluoro-1-trifluoromethyl-propyl)phenylamine (51.6 g, 61.1% yield). $^1$H NMR (400 MHz, CDCl$_3$): 7.58 (s, 2H), 4.90 (bs, 2H).

Example I2

N-[2,6-dibromo-4-(1,2,2,3,3,3-hexafluoro-1-trifluoromethylpropyl)phenyl]-3-nitro-4-(1,2,4-triazol-1-yl)benzamide (Compound No. A4 of Table A)

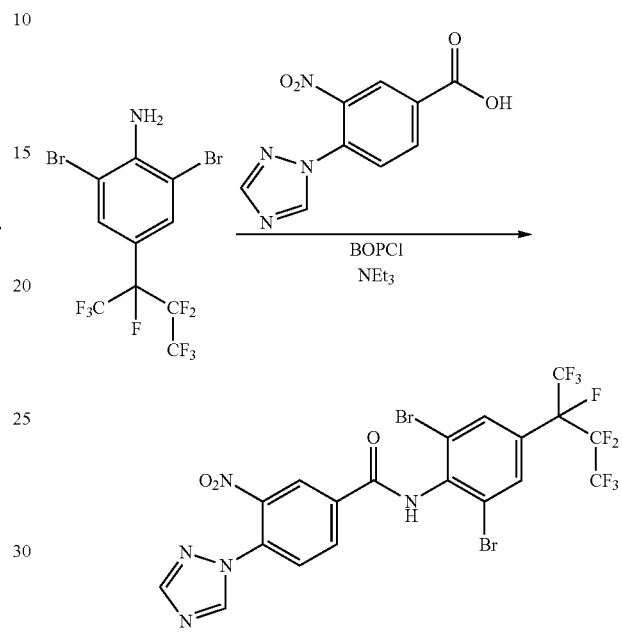

To a suspension of 2,6-dibromo-4-(1,2,2,3,3,3-hexafluoro-1-trifluoromethylpropyl)-phenylamine (Example I1) (635 mg, 1.35 mmol) in 1,2-dichloroethane (6.5 ml) was added triethylamine (0.57 ml, 4.06 mmol), followed by 3-nitro-4-(1H-1,2,4-triazol-1-yl)benzoic acid (634 mg, 2.7 mmol) and bis(2-oxo-3-oxazolidinyl)phosphonic chloride ("BOP—Cl") (689 mg, 2.7 mmol). The reaction mixture was stirred at reflux for 16 hours. The progress of the reaction was followed by thin layer chromatography and, because it was necessary in this case, further doses of 3-nitro-4-(1H-1,2,4-triazol-1-yl) benzoic acid (4×0.675 mmol), bis(2-oxo-3-oxazolidinyl) phosphonic chloride (4×1.35 mmol) and triethylamine (4×1.35 mmol) were added over the course of 48 hours. The reaction was quenched by addition of aqueous hydrochloric acid (1M) and the phases were separated. The organic phase was washed with saturated aqueous sodium hydrogen carbonate, dried over sodium sulfate and concentrated. The residue was purified by column chromatography on silica gel (eluent: cyclohexane/ethyl acetate 1:2) to give Compound No. A4 of Table A (605 mg, 65% yield).

The following compounds were prepared by analogous methods:

N-[2-Ethyl-4-(1,2,2,3,3,3-hexafluoro-1-trifluoromethylpropyl)-6-methylphenyl]-3-nitro-4-(1,2,4-triazol-1-yl)benzamide (Compound No. A3 of Table A).

N-[2,6-Diethyl-4-(1,2,2,2-tetrafluoro-1-trifluoromethylethyl)phenyl]-3-nitro-4-(1,2,4-triazol-1-yl)benzamide (Compound No. A2 of Table A), using dichloromethane as solvent.

N-[2,6-Dimethyl-4-(1,2,2,2-tetrafluoro-1-trifluoromethylethyl)phenyl]-3-nitro-4-(1,2,4-triazol-1-yl)benzamide (Compound No. A1 of Table A), using dichloromethane as solvent.

Example I3

3-amino-N-[2,6-dibromo-4-(1,2,2,3,3,3-hexafluoro-1-trifluoromethylpropyl)-phenyl]-4-(1,2,4-triazol-1-yl)benzamide (Compound No. B4 of Table B)

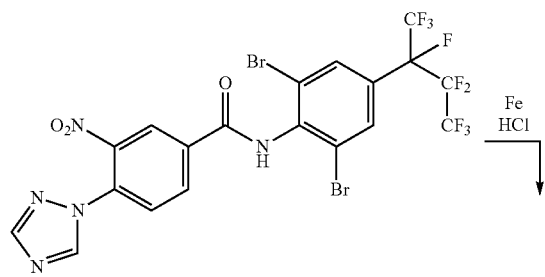

To a solution of N-[2,6-dibromo-4-(1,2,2,3,3,3-hexafluoro-1-trifluoromethylpropyl)-phenyl]-3-nitro-4-(1,2,4-triazol-1-yl)benzamide (Example I2) (675 mg, 0.98 mmol) in a mixture of ethanol and water (20 ml and 4 ml, respectively) was added aqueous hydrochloric acid (37% w/v) (0.25 ml) and iron metal powder (5550 mg, 9.8 mmol). The reaction mixture was stirred at 80° C. for 1 hour. The mixture was filtered through a silica gel pad and the filtrate concentrated. The residue was purified by column chromatography on silica gel (eluent: cyclohexane/ethyl acetate 1:1) to give Compound No. B4 of Table B (372 mg, 58% yield).

The following compound was prepared by an analogous method:
3-Amino-N-[2-ethyl-4-(1,2,2,3,3,3-hexafluoro-1-trifluoromethylpropyl)-6-methyl-phenyl]-4-(1,2,4-triazol-1-yl)benzamide (Compound No. B3 of Table B).

Example I4

3-amino-N-[2,6-diethyl-4-(1,2,2,2-tetrafluoro-1-trifluoromethylethyl)phenyl]-4-(1,2,4-triazol-1-yl)benzamide (Compound No. B2 of Table B)

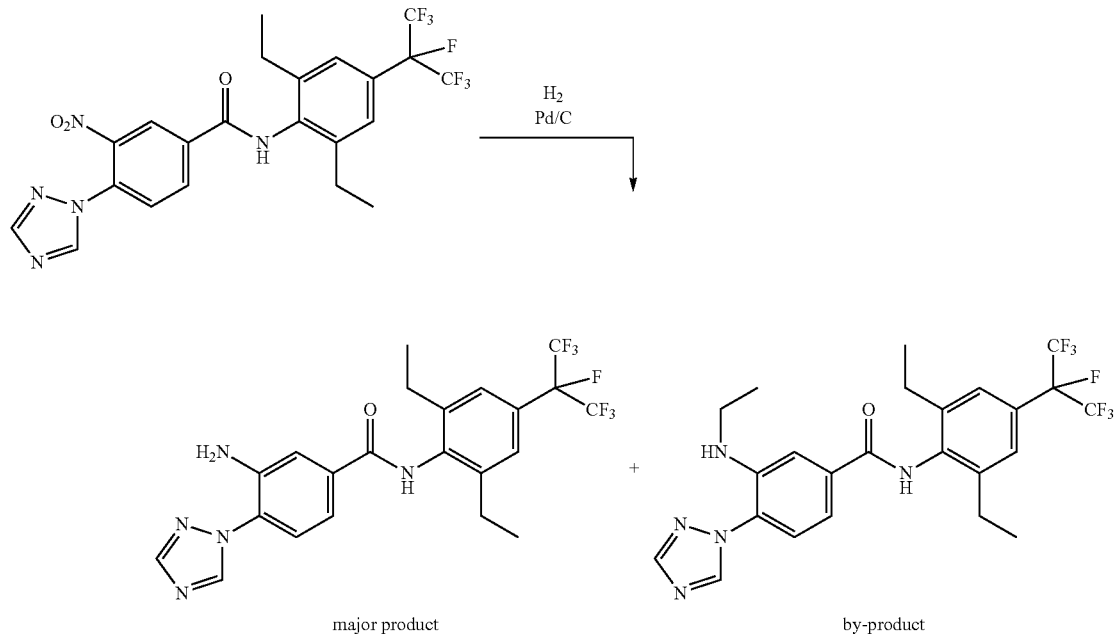

A solution of N-[2,6-diethyl-4-(1,2,2,2-tetrafluoro-1-trifluoromethylethyl)phenyl]-3-nitro-4-(1,2,4-triazol-1-yl)benzamide (473 mg, 0.89 mmol) (Example I2) in ethanol (9 ml) was charged with palladium on carbon (10%) (140 mg, 0.13 mmol) and was stirred under a atmosphere of hydrogen for 15 hours. The reaction mixture was filtered and the filtrate was concentrated. The residue was purified by column chromatography on silica gel (eluent: cyclohexane/ethyl acetate 1:4) to give Compound No. B2 of Table B (328 mg, 74% yield) and Compound No. C1 of Table C (18 mg, 4% yield).

The following compound was prepared by an analogous method:
3-Amino-N-[2,6-dimethyl-4-(1,2,2,2-tetrafluoro-1-trifluoromethylethyl)phenyl]-4-(1,2,4-triazol-1-yl)benzamide (Compound No. B1 of Table B).

Example P1

3-(4-cyanobenzoylamino)-N-[2,6-dibromo-4-(1,2,2,3,3,3-hexafluoro-1-trifluoromethylpropyl)phenyl]-4-(1,2,4-triazol-1-yl)benzamide (Compound No. D8 of Table D)

The following compounds were prepared by analogous methods:

3-(2-Methyl-3-nitrobenzoylamino)-N-[2-ethyl-4-(1,2,2,3,3,3-hexafluoro-1-trifluoromethylpropyl)-6-methylphenyl]-4-(1,2,4-triazol-1-yl)benzamide (Compound No. D3 of Table D).

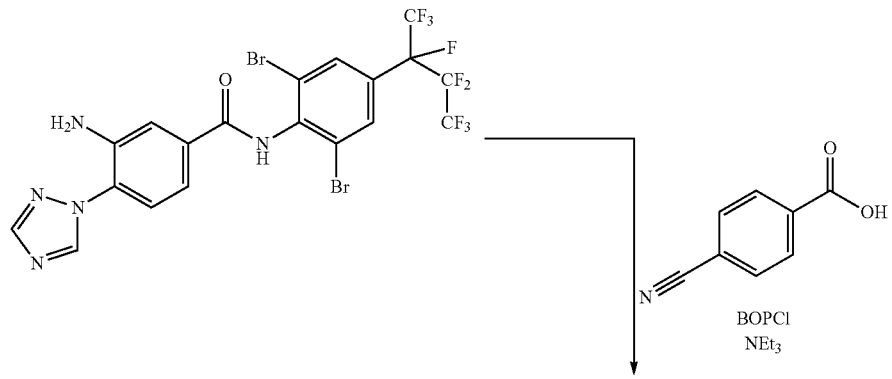

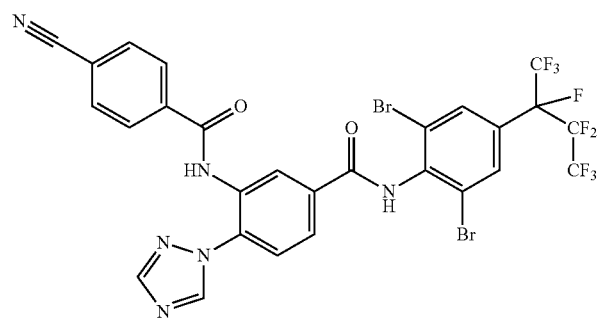

To a suspension of 3-amino-N-[2,6-dibromo-4-(1,2,2,3,3,3-hexafluoro-1-trifluoro-methylpropyl)phenyl]-4-(1,2,4-triazol-1-yl)benzamide (Example I3) (30 mg, 0.046 mmol) in tetrahydrofuran (1.2 ml) was added triethylamine (19 µl, 0.13 mmol), followed by 4-cyanobenzoic acid (13.5 mg, 0.09 mmol) and bis(2-oxo-3-oxazolidinyl)phosphonic chloride ("BOP—Cl") (23.3 mg, 0.09 mmol). The reaction mixture was stirred at reflux for 16 hours. The reaction was quenched by addition of aqueous hydrochloric acid (1M) and the phases were separated. The organic phase was washed with saturated aqueous sodium hydrogen carbonate, dried over sodium sulfate and concentrated. The residue was purified by column chromatography on silica gel (eluent: cyclohexane/ethyl acetate 1:1) to give Compound No. D8 of Table D (25 mg, 70% yield).

3-(2-Chloro-4-fluorobenzoylamino)-N-[2-ethyl-4-(1,2,2,3,3,3-hexafluoro-1-trifluoromethylpropyl)-6-methylphenyl]-4-(1,2,4-triazol-1-yl)benzamide (Compound No. D4 of Table D).

3-(4-Cyanobenzoylamino)-N-[2-ethyl-4-(1,2,2,3,3,3-hexafluoro-1-trifluoromethyl-propyl)-6-methylphenyl]-4-(1,2,4-triazol-1-yl)benzamide (Compound No. D5 of Table D).

3-(2-Chloro-4-fluorobenzoylamino)-N-[2,6-dibromo-4-(1,2,2,3,3,3-hexafluoro-1-trifluoromethylpropyl)phenyl]-4-(1,2,4-triazol-1-yl)benzamide (Compound No. D9 of Table D).

3-(2-Methyl-3-nitrobenzoylamino)-N-[2,6-dibromo-4-(1,2,2,3,3,3-hexafluoro-1-trifluoromethylpropyl)phenyl]-4-(1,2,4-triazol-1-yl)benzamide (Compound No. D10 of Table D).

Example P2

3-(4-fluorobenzoylamino)-N-[2,6-diethyl-4-(1,2,2,2-tetrafluoro-1-trifluoromethylethyl)phenyl]-4-(1,2,4-triazol-1-yl)benzamide (Compound No. D2 of Table D)

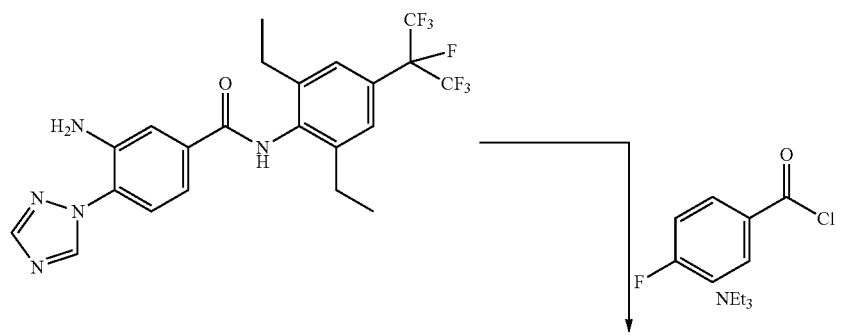

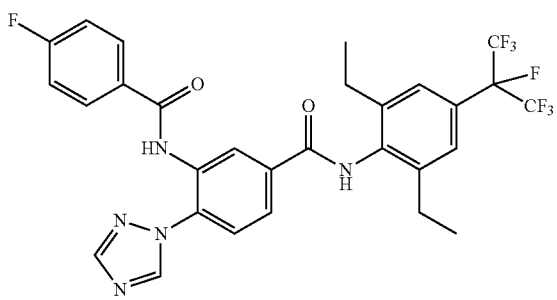

To a solution of 3-amino-N-[2,6-diethyl-4-(1,2,2,2-tetrafluoro-1-trifluoromethyl-ethyl)phenyl]-4-(1,2,4-triazol-1-yl)benzamide (75 mg, 0.15 mmol) (Example I4) in dichloromethane (3 ml) was added triethylamine (63 µl, 0.45 mmol) and 4-fluorobenzoyl chloride (21.3 µl, 0.18 mmol). The reaction mixture was heated to reflux for 15 hours. The reaction mixture was cooled to ambient temperature and quenched by addition of saturated aqueous sodium hydrogen carbonate (5 ml). The phases were separated and the aqueous phase was extracted with dichloromethane (2×5 ml). The combined organic phases were dried over sodium sulfate and concentrated. The residue was purification by column chromatography on silica gel (eluent: hexane/ethyl acetate 1:4) to give Compound No. D2 of Table D (76 mg, 82% yield).

The following compounds were prepared by analogous methods:

3-(4-Fluorobenzoylamino)-N-[2,6-dimethyl-4-(1,2,2,2-tetrafluoro-1-trifluoromethyl-ethyl)phenyl]-4-(1,2,4-triazol-1-yl)benzamide (Compound No. D1 of Table D).

3-(4-Fluorobenzoylamino)-N-[2-ethyl-4-(1,2,2,3,3,3-hexafluoro-1-trifluoromethyl-propyl)-6-methylphenyl]-4-(1,2,4-triazol-1-yl)benzamide (Compound No. D6 of Table D), using tetrahydrofuran as solvent.

3-(4-Fluorobenzoylamino)-N-[2,6-dibromo-4-(1,2,2,3,3,3-hexafluoro-1-trifluoromethylpropyl)phenyl]-4-(1,2,4-triazol-1-yl)benzamide (Compound No. D7 of Table D), using tetrahydrofuran as solvent.

TABLE A

Compounds of formula (Ia) wherein $G^2$ is oxygen and $R^2$ is hydrogen.

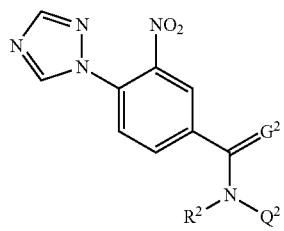

(Ia)

| Comp. No. | $Q^2$ | RT (min) | MH+ | LC-MS method |
|---|---|---|---|---|
| A1 | 2,6-dimethyl-4-(heptafluoroprop-2-yl)phenyl | 1.94 | 506 | D |
| A2 | 2,6-diethyl-4-(heptafluoroprop-2-yl)phenyl | 2.05 | 534 | 4 |
| A3 | 2-ethyl-6-methyl-4-(nonafluorobut-2-yl)phenyl | 2.07 | 570 | 2 |
| A4 | 2,6-dibromo-4-(nonafluorobut-2-yl)phenyl | 2.05 | 686 | 2 |

TABLE B

Compounds of formula (Ib) where $G^2$ is oxygen and $R^2$ is hydrogen.

(Ib)

| Comp. No. | $Q^2$ | RT (min) | MH⁺ | LC-MS method |
|---|---|---|---|---|
| B1 | 2,6-dimethyl-4-(heptafluoroprop-2-yl)phenyl | 1.84 | 476 | D |
| B2 | 2,6-diethyl-4-(heptafluoroprop-2-yl)phenyl | 2.03 | 504 | 4 |
| B3 | 2-ethyl-6-methyl-4-(nonafluorobut-2-yl)phenyl | 1.98 | 540 | 2 |
| B4 | 2,6-dibromo-4-(nonafluorobut-2-yl)phenyl | 1.96 | 656 | 2 |

TABLE C

Compounds of formula (Ic) where $G^2$ is oxygen, $R^1$ is ethyl, $R^2$ is hydrogen and $Q^2$ is 2,6-diethyl-4-(heptafluoroprop-2-yl)phenyl.

(Ic)

| Comp. No. | RT (min) | MH⁺ | LC-MS method |
|---|---|---|---|
| C1 | 2.15 | 532 | 4 |

TABLE D

Compounds of formula (Id) where $G^1$ and $G^2$ are oxygen and $R^1$ and $R^2$ are hydrogen.

(Id)

| Comp. No. | $Q^1$ | $Q^2$ | RT (min) | MH⁺ | LC-MS Method |
|---|---|---|---|---|---|
| D1 | 4-fluorophenyl | 2,6-dimethyl-4-(heptafluoroprop-2-yl)phenyl | 2.08 | 598 | 4 |
| D2 | 4-fluorophenyl | 2,6-diethyl-4-(heptafluoroprop-2-yl)phenyl | 2.12 | 626 | 4 |
| D3 | 2-methyl-3-nitrophenyl | 2-ethyl-6-methyl-4-(nonafluorobut-2-yl)phenyl | 2.12 | 703 | 2 |
| D4 | 2-chloro-4-fluorophenyl | 2-ethyl-6-methyl-4-(nonafluorobut-2-yl)phenyl | 2.14 | 696 | 2 |
| D5 | 4-cyanophenyl | 2-ethyl-6-methyl-4-(nonafluorobut-2-yl)phenyl | 2.11 | 669 | 2 |
| D6 | 4-fluorophenyl | 2-ethyl-6-methyl-4-(nonafluorobut-2-yl)phenyl | 2.16 | 662 | 2 |
| D7 | 4-fluorophenyl | 2,6-dibromo-4-(nonafluorobut-2-yl)phenyl | 2.15 | 778 | 2 |
| D8 | 4-cyanophenyl | 2,6-dibromo-4-(nonafluorobut-2-yl)phenyl | 2.05 | 785 | 2 |
| D9 | 2-chloro-4-fluorophenyl | 2,6-dibromo-4-(nonafluorobut-2-yl)phenyl | 2.09 | 812 | 2 |
| D10 | 2-methyl-3-nitrophenyl | 2,6-dibromo-4-(nonafluorobut-2-yl)phenyl | 2.12 | 819 | 2 |

Biological Examples

These Examples illustrate the insecticidal and acaricidal properties of the compounds of formula (I). The tests were performed as follows:

*Spodoptera* Littoralis (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of *Spodoptera littoralis*: A1, A2, A3, A4, B2, B3, B4, C1, D1, D2, D3, D4, D5, D6, D7, D8, D9, D10.

*Heliothis Virescens* (Tobacco Budworm):

Eggs (0-24 h old) were placed in 24-well microtiter plate on artificial diet and treated with test solutions at an application rate of 200 ppm (concentration in well 18 ppm) by pipetting.

After an incubation period of 4 days, samples were checked for egg mortality, larval mortality, and growth regulation.

The following compound gave at least 80% control of *Heliothis virescens*: A1, A3, A4, B1, B2, B3, B4, C1, D1, D2, D3, D4, D5, D6, D7, D8, D9, D10.

*Plutella Xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compound gave at least 80% control of *Plutella xylostella*: A1, A3, A4, B2, B3, B4, C1, D1, D2, D3, D4, D5, D6, D7, D8, D9, D10.

*Diabrotica Balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of *Diabrotica balteata*: A1, A2, A3, A4, B2, B3, C1, D1, D2, D4, D6, D7, D8, D9, D10.

*Thrips Tabaci* (Onion Thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci*: A3, A4, D2, D4, D6, D7, D8, D9, D10.

*Tetranychus Urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*: A1, A3, A4, B1, B2, B3, B4, D3, D4, D6, D9, D10.

The invention claimed is:

1. A compound of formula (I) wherein

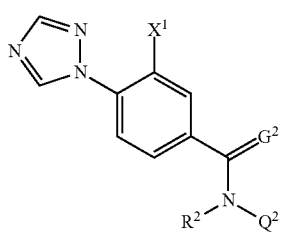

(I)

$X^1$ is $NO_2$, $NH_2$, a group of formula (II) or a group of formula (III)

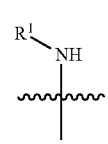

(II)

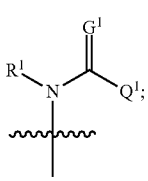

(III)

$G^1$ and $G^2$ are each independently oxygen or sulfur;
$Q^1$ is aryl or heterocyclyl, each optionally substituted by one to five $R^3$ substituents, which may be the same or different;
$R^1$ is hydrogen, $C_1$-$C_8$alkyl, $C_1$-$C_8$alkylcarbonyl, or $C_1$-$C_8$alkoxycarbonyl;
$R^2$ is hydrogen, $C_1$-$C_8$alkyl, $C_1$-$C_8$alkylcarbonyl, or $C_1$-$C_8$alkoxycarbonyl;
$R^3$ is halogen, cyano, nitro, $C_1$-$C_4$alkyl, $C_1$-$C_4$haloalkyl, $C_1$-$C_4$alkoxy, or $C_1$-$C_4$haloalkoxy;
$Q^2$ is a group of formula (IV)

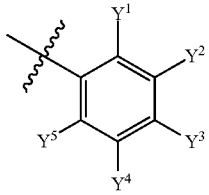

(IV)

$Y^1$ and $Y^5$ are each independently selected from halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkoxy-$C_1$-$C_4$alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl or $C_1$-$C_3$haloalkylsulfonyl;
$Y^3$ is selected from $C_2$-$C_6$perfluoroalkyl, $C_2$-$C_6$perfluorocycloalkyl, hydroxy-$C_2$-$C_6$perfluoroalkyl, $C_1$-$C_4$alkylcarbonyloxy-$C_2$-$C_6$perfluoroalkyl, $C_1$-$C_4$haloalkylcarbonyloxy-$C_2$-$C_6$perfluoroalkyl, $C_1$-$C_6$perfluoroalkylthio, $C_1$-$C_6$perfluoroalkylsulfinyl, $C_1$-$C_6$perfluoro-alkylsulfonyl, arylcarbonyloxy-$C_2$-$C_6$perfluoroalkyl, and arylcarbonyloxy-$C_2$-$C_6$perfluoroalkyl in which the aryl group may be substituted by one to five $R^4$ groups, which may be the same or different;
$Y^2$ and $Y^4$ are each independently selected from hydrogen, halogen and $C_1$-$C_4$alkyl; and
$R^4$ is halogen, cyano, nitro, $C_1$-$C_4$alkyl, $C_1$-$C_4$haloalkyl, $C_1$-$C_4$alkoxy or $C_1$-$C_4$haloalkoxy;
or an agrochemically acceptable salt or N-oxides thereof.

2. A compound according to claim 1 wherein $G^1$ and $G^2$ are both oxygen.

3. A compound according to either claim 1 wherein $Q^1$ is selected from phenyl, biphenyl and a five to six-membered monocyclic heteroaryl group containing 1, 2 or 3 heteroatoms independently selected from nitrogen, oxygen and sulfur; each optionally substituted by one to five $R^3$ substituents, which may be the same or different.

4. A compound according to claim 3 wherein $Q^1$ is phenyl, optionally substituted by one to three $R^3$ substituents, which may be the same or different, selected from cyano, nitro, fluoro, chloro, bromo, iodo, methyl, ethyl, isopropyl, tert-butyl, trifluoromethyl, methoxy and trifluoromethoxy.

5. A compound according to claim 1 wherein $R^1$ is hydrogen, methyl or ethyl.

6. A compound according to claim 1 wherein $R^2$ is hydrogen.

7. A compound according to claim 1 wherein $Q^2$ is 2,6-dimethyl-4-(heptafluoroprop-2-yl)phenyl, 2,6-diethyl-4-(heptafluoroprop-2-yl)phenyl, 2-ethyl-6-methyl-4-(nonafluorobut-2-yl)phenyl, 2,6-dibromo-4-(nonafluorobut-2-yl)phenyl, 2-bromo-6-chloro-4-(nonafluoro-but-2-yl)phenyl, or 2,6-dichloro-4-(nonafluoro-but-2-yl)phenyl.

8. A compound according to claim 1, which is selected from

N-[2,6-dibromo-4-(1,2,2,3,3,3-hexafluoro-1-trifluoromethylpropyl)phenyl]-3-nitro-4-(1,2,4-triazol-1-yl)benzamide;

3-amino-N-[2,6-dibromo-4-(1,2,2,3,3,3-hexafluoro-1-trifluoromethylpropyl)-phenyl]-4-(1,2,4-triazol-1-yl)benzamide;

3-(4-cyanobenzoylamino)-N-[2,6-dibromo-4-(1,2,2,3,3,3-hexafluoro-1-trifluoromethylpropyl)phenyl]-4-(1,2,4-triazol-1-yl)benzamide;

3-(2-methyl-3-nitrobenzoylamino)-N-[2-ethyl-4-(1,2,2,3,3,3-hexafluoro-1-trifluoromethylpropyl)-6-methylphenyl]-4-(1,2,4-triazol-1-yl)benzamide;

3-(2-chloro-4-fluorobenzoylamino)-N-[2-ethyl-4-(1,2,2,3,3,3-hexafluoro-1-trifluoromethylpropyl)-6-methylphenyl]-4-(1,2,4-triazol-1-yl)benzamide;

3-(4-cyanobenzoylamino)-N-[2-ethyl-4-(1,2,2,3,3,3-hexafluoro-1-trifluoromethyl-propyl)-6-methylphenyl]-4-(1,2,4-triazol-1-yl)benzamide;

3-(2-chloro-4-fluorobenzoylamino)-N-[2,6-dibromo-4-(1,2,2,3,3,3-hexafluoro-1-trifluoromethylpropyl)phenyl]-4-(1,2,4-triazol-1-yl)benzamide;

3-(2-methyl-3-nitrobenzoylamino)-N-[2,6-dibromo-4-(1,2,2,3,3,3-hexafluoro-1-trifluoromethylpropyl)phenyl]-4-(1,2,4-triazol-1-yl)benzamide;

3-(4-fluorobenzoylamino)-N-[2,6-diethyl-4-(1,2,2,2-tetrafluoro-1-trifluoromethylethyl)phenyl]-4-(1,2,4-triazol-1-yl)benzamide;

3-(4-fluorobenzoylamino)-N-[2,6-dimethyl-4-(1,2,2,2-tetrafluoro-1-trifluoromethyl-ethyl)phenyl]-4-(1,2,4-triazol-1-yl)benzamide;

3-(4-fluorobenzoylamino)-N[2-ethyl-4-(1,2,2,3,3,3-hexafluoro-1-trifluoromethyl-propyl)-6-methylphenyl]-4-(1,2,4-triazol-1-yl)benzamide; and 3-(4-fluorobenzoylamino)-N-[2,6-dibromo-4-(1,2,2,3,3,3-hexafluoro-1-trifluoromethylpropyl)phenyl]-4-(1,2,4-triazol-1-yl)benzamide.

9. A method of controlling at least one pest selected from the group consisting of insects, acarines, nematodes, and molluscs which comprises applying to said pest(s), to a locus of said pest(s), or to a plant susceptible to attack by said pest(s), a compound of formula (I) as defined in claim 1.

10. An insecticidal, acaricidal, nematicidal or molluscicidal composition comprising a compound of formula (I) as defined in claim 1 together with an agrochemically acceptable diluent or carrier.

11. A composition according to claim 10 which further comprises one or more additional insecticidal, acaricidal, nematicidal or molluscicidal compounds.

* * * * *

UNITED STATES PATENT AND TRADEMARK OFFICE
CERTIFICATE OF CORRECTION

PATENT NO. : 8,455,399 B2
APPLICATION NO. : 13/318946
DATED : June 4, 2013
INVENTOR(S) : Maienfisch et al.

It is certified that error appears in the above-identified patent and that said Letters Patent is hereby corrected as shown below:

In the Claims

Column 29, in claim 1, line 30, remove "wherein" before chemical structure (I)

Column 29, in claim 1, line 43, insert --wherein-- following chemical structure (I)

Column 30, in claim 3, line 43, remove "either" before "claim 1"

Signed and Sealed this
Twelfth Day of November, 2013

Teresa Stanek Rea
*Deputy Director of the United States Patent and Trademark Office*